(12) United States Patent
West

(10) Patent No.: US 10,625,055 B2
(45) Date of Patent: Apr. 21, 2020

(54) METHOD AND APPARATUS FOR TRACKING A POSITION OF A MEDICAL DEVICE

(71) Applicant: THE CLEVELAND CLINIC FOUNDATION, Cleveland, OH (US)

(72) Inventor: Karl West, Cleveland, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 897 days.

(21) Appl. No.: 14/749,677

(22) Filed: Jun. 25, 2015

(65) Prior Publication Data

US 2015/0374523 A1    Dec. 31, 2015

Related U.S. Application Data

(60) Provisional application No. 62/017,468, filed on Jun. 26, 2014.

(51) Int. Cl.

| | |
|---|---|
| *A61B 5/06* | (2006.01) |
| *A61M 25/09* | (2006.01) |
| *A61F 2/966* | (2013.01) |
| *A61B 5/00* | (2006.01) |
| *A61F 2/95* | (2013.01) |
| *A61F 2/97* | (2013.01) |
| *A61B 34/20* | (2016.01) |

(52) U.S. Cl.
CPC .............. *A61M 25/09* (2013.01); *A61B 5/067* (2013.01); *A61B 5/6851* (2013.01); *A61B 5/6886* (2013.01); *A61F 2/966* (2013.01); *A61B 2034/2046* (2016.02); *A61B 2034/2051* (2016.02); *A61F 2/97* (2013.01); *A61F 2002/9522* (2013.01); *A61M 2025/09125* (2013.01)

(58) Field of Classification Search
CPC ..................................................... A61B 5/067
See application file for complete search history.

(56) References Cited

U.S. PATENT DOCUMENTS

| | | | |
|---|---|---|---|
| 6,371,971 B1 | 4/2002 | Tsugita et al. | |
| 8,208,991 B2* | 6/2012 | Markowitz | A61B 5/0422 600/424 |
| 2006/0074318 A1* | 4/2006 | Ahmed | A61B 5/02158 600/465 |
| 2009/0157052 A1 | 6/2009 | Verbitsky et al. | |
| 2013/0296692 A1* | 11/2013 | Vanney | A61M 25/09 600/424 |

* cited by examiner

*Primary Examiner* — Rochelle D Turchen
(74) *Attorney, Agent, or Firm* — Tarolli, Sundheim, Covell & Tummino LLP

(57) ABSTRACT

A trackable guidewire apparatus and method for use are described. Longitudinally spaced proximal and distal guidewire ends are separated by a guidewire body. A plurality of longitudinally spaced position sensors are configured to provide signals corresponding to a three-dimensional position of at least one position sensor in a coordinate system of an associated tracking system in response to an electromagnetic field/stimulus. At least one retention mechanism is provided for maintaining the medical device in a predetermined retention position longitudinally along the guidewire body. At least one stop structure is provided in a predetermined stop position longitudinally along the guidewire body.

19 Claims, 7 Drawing Sheets

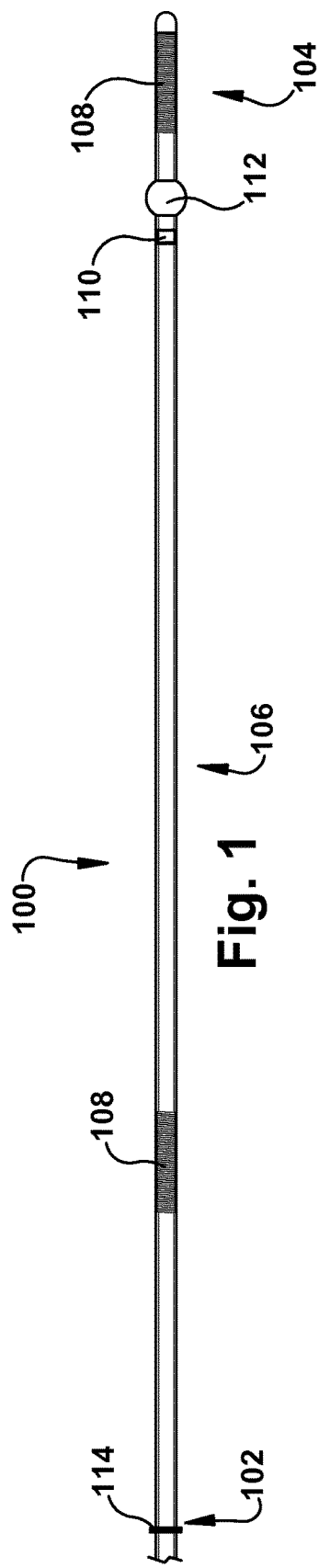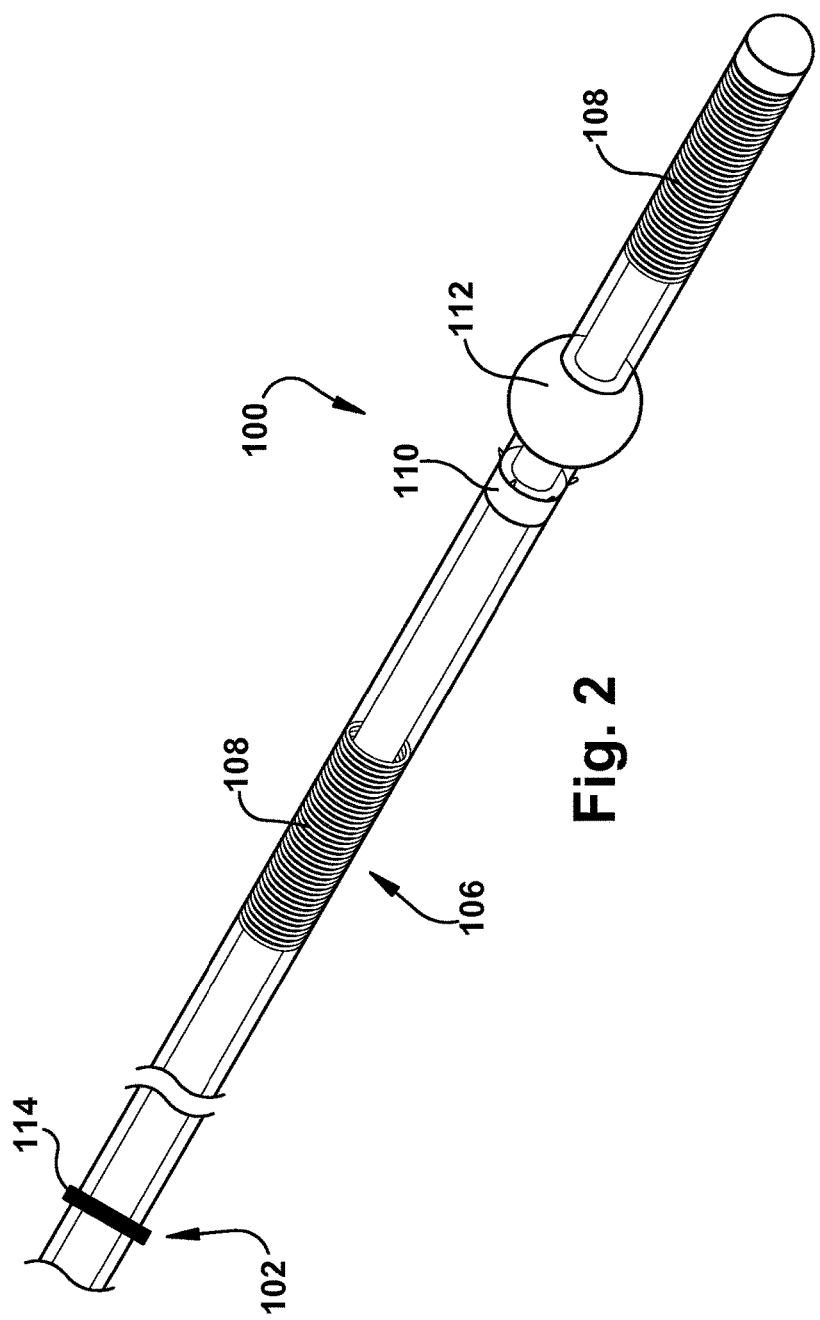

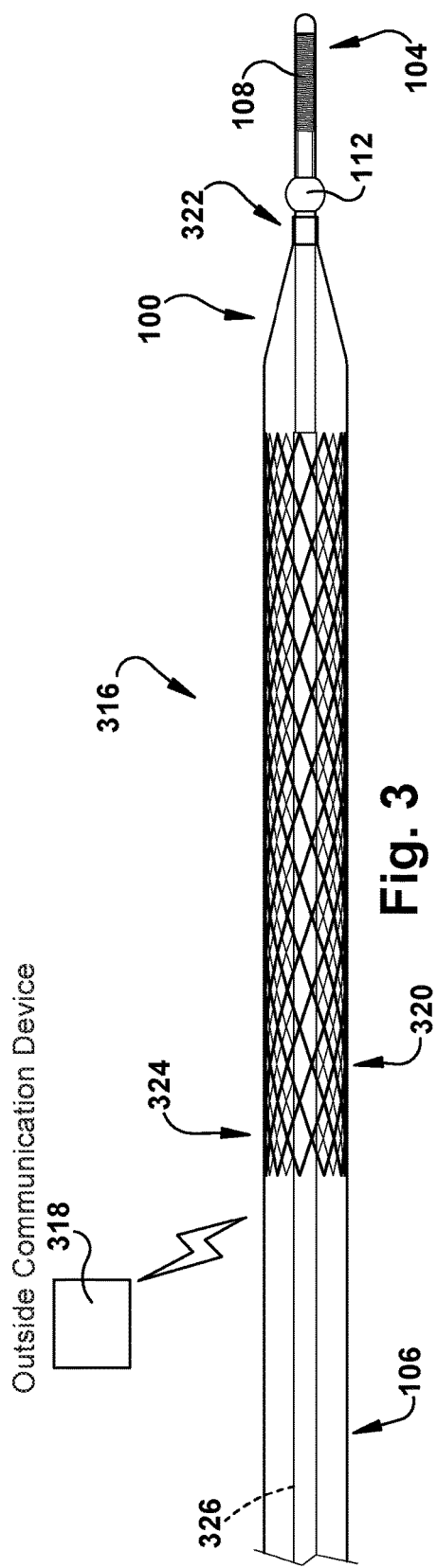
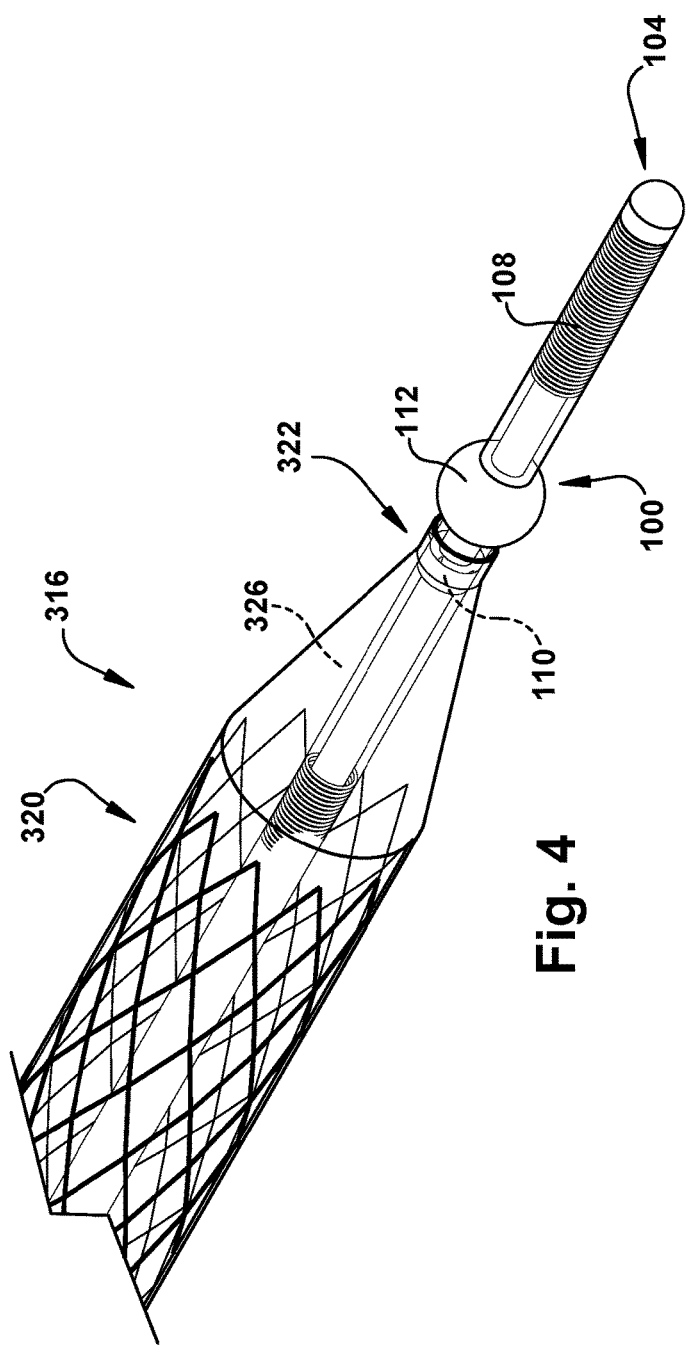
Fig. 3
Fig. 4

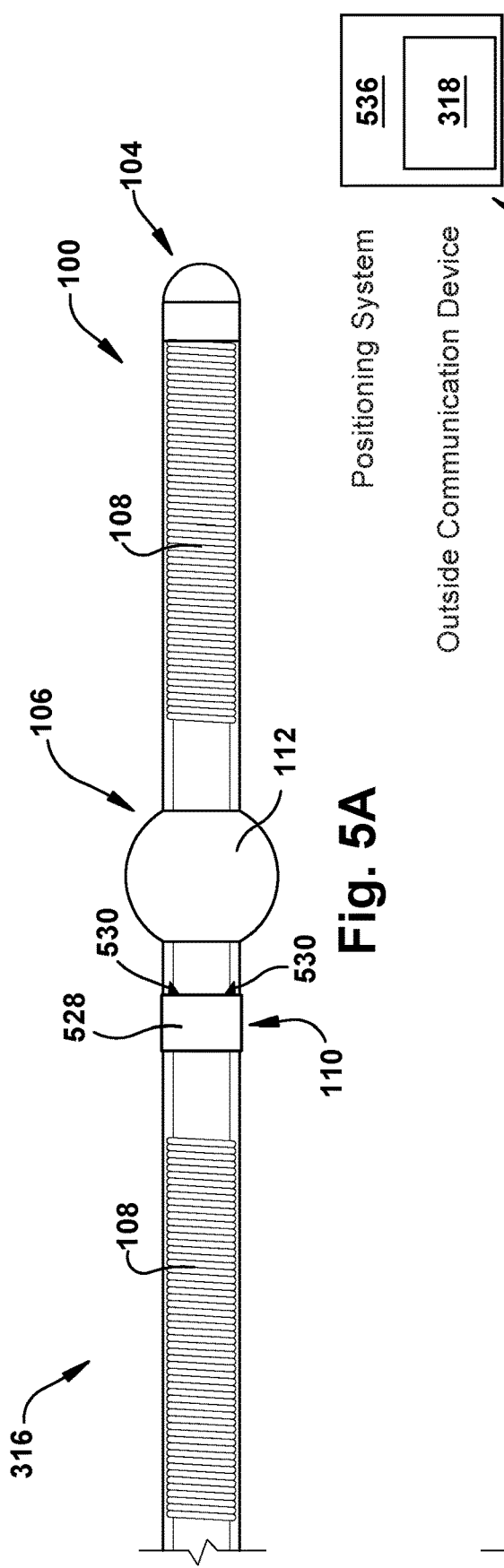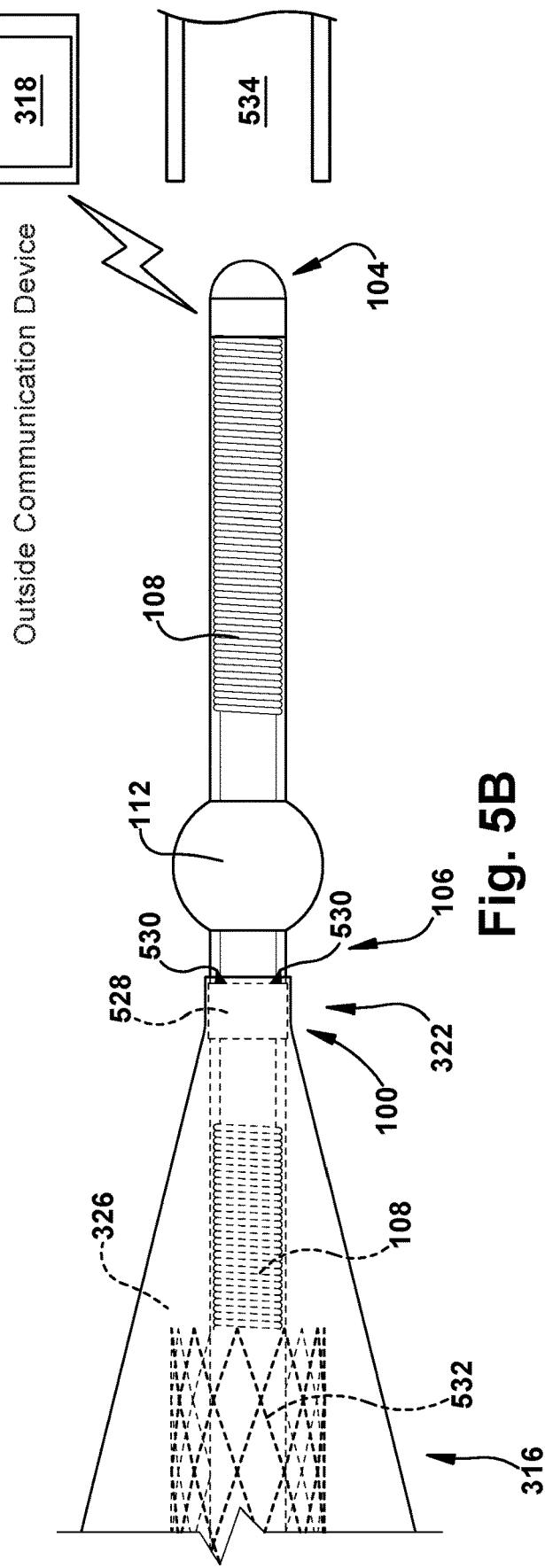

METHOD AND APPARATUS FOR TRACKING A POSITION OF A MEDICAL DEVICE

RELATED APPLICATION

This application claims priority from U.S. Provisional Application No. 62/017,468, filed 26 Jun. 2014, the subject matter of which is incorporated herein by reference in its entirety.

TECHNICAL FIELD

This disclosure relates to an apparatus and method for tracking a position of a medical device and, more particularly, to a method and apparatus for tracking a position of a medical device relative to a target site of a patient lumen.

BACKGROUND

During a surgical procedure, a surgeon or other medical professional (hereafter, "user") may desire to place a medical device, of any type, into a predetermined position with respect to a patient tissue. The user may wish to achieve the desired placement in a relatively precise manner. For example, during placement of a stent, graft, stent-graft, or other medical prosthesis (hereafter referenced generically as a "stent") across an aortic aneurysm using a delivery catheter or guidewire, it may be desirable to orient the stent within the blood vessel (a body lumen) such that the stent is substantially centered within the vessel (as viewed across a lateral cross-section of the vessel), with each end of the stent being located longitudinally adjacent a non-aneurytic portion of the blood vessel upstream and downstream, respectively, from the aneurysm. (In this example, the body of the stent will "bridge" across/through the aneurysm to maintain a bloodflow channel therethrough which is substantially similar in cross-sectional area to the non-aneurytic neighbouring portions of the blood vessel.)

Because of the relative difficulty in placing a medical device precisely during a closed (percutaneous) medical procedure, a user will often consult an intraoperative imaging system (e.g., x-ray fluoroscopy) to periodically "check" the position of the medical device as it is moved toward the desired target site by a delivery device. However, commonly used intraoperative imaging devices may require that the procedure be paused during image acquisition, thus lengthening the total operative time. In addition, radiopaque markers or components may be required on the medical device and/or the delivery device to enable intraoperative tracking—the radiopaque components might not represent a preferred design path for the device, though, absent the need to facilitate imaging. Finally, certain types of imaging systems are magnetically sensitive, requiring the provision of specialized, largely non-magnetic medical devices and/or delivery devices to avoid negative side effects.

SUMMARY

In an embodiment, a method of tracking a position of a medical device relative to a target site of a patient lumen is described. A trackable guidewire is provided. The guidewire has longitudinally spaced proximal and distal guidewire ends separated by a guidewire body. The guidewire includes a plurality of longitudinally spaced position sensors configured to provide signals corresponding to a three-dimensional position in space to an outside communication device. The guidewire includes at least one retention mechanism for maintaining a medical device in a predetermined retention position longitudinally along the guidewire body. The guidewire includes at least one stop structure in a predetermined stop position longitudinally along the guidewire body. The medical device is placed in the retention position. The medical device is maintained in the retention position via the retention mechanism. The distal guidewire end is placed into the patient lumen. The distal guidewire end and at least a portion of the guidewire body are advanced through at least a portion of the patient lumen. A three-dimensional position of at least one position sensor in a coordinate system of an associated tracking system is determined. A relative position of the at least one sensor with respect to geometry of the patient lumen is determined.

In an embodiment, a trackable guidewire apparatus is described. Longitudinally spaced proximal and distal guidewire ends are separated by a guidewire body. A plurality of longitudinally spaced position sensors are configured to provide signals corresponding to a three-dimensional position of at least one position sensor in a coordinate system of an associated tracking system in response to an electromagnetic field/stimulus. At least one retention mechanism is provided for maintaining the medical device in a predetermined retention position longitudinally along the guidewire body. At least one stop structure is provided in a predetermined stop position longitudinally along the guidewire body.

BRIEF DESCRIPTION OF THE DRAWINGS

For a better understanding of the disclosure, reference may be made to the accompanying drawings, in which:

FIG. 1 is a partial side view of one embodiment of an apparatus in a first configuration;

FIG. 2 is a perspective side view of the embodiment of FIG. 1;

FIG. 3 is a partial side view of the embodiment of FIG. 1 in a second configuration;

FIG. 4 is a perspective side view of the embodiment of FIG. 3;

FIGS. 5A-5B schematically depict a partial sequence of operation of the embodiment of FIG. 1.

Figure 6A:
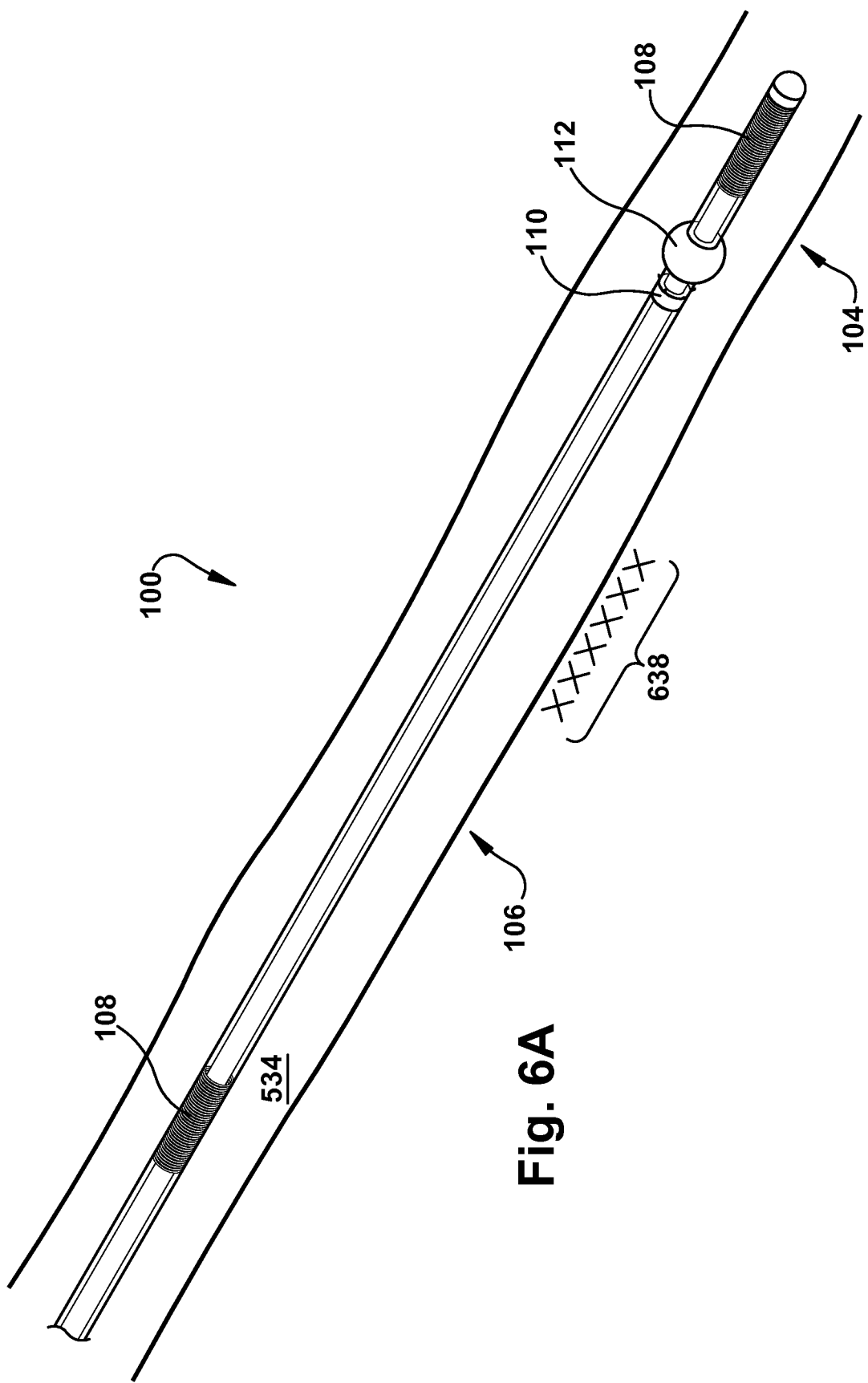
FIGS. 6A-6D schematically depict a partial sequence of operation of the embodiment of FIG. 1.

This application also includes an Appendix that forms an integral part of this disclosure.

DESCRIPTION OF EMBODIMENTS

FIGS. 1-2 depict a trackable guidewire apparatus 100 including longitudinally spaced proximal and distal guidewire ends 102 and 104, respectively, separated by a guidewire body 106. A plurality of longitudinally spaced position sensors 108 are arranged at predetermined positions along the guidewire body 106, with the sensors being active and/or passive, as desired for a particular use environment. For example, at least one of the sensors 108 could include one or more accelerometers, optionally coupled with appropriate power source(s), transmitter(s), and/or processor(s) to actively track a relative or absolute sensor position. As another example, at least one of the sensors 108 could include an RFID tag or other passive component(s) that can be interrogated by an outside device (not shown in FIG. 1) to produce an indication of a relative or absolute sensor position. As discussed herein, it will be presumed that at least one sensor 108 is configured to provide signals that can be employed to determine a three-dimensional position of the sensor in space, such as in a coordinate system of an associated tracking system, as will be discussed herein. For example, each sensor can include a coil of an electrically conductive material that can provide a sensor signal (e.g., an induced current) in response to an electromagnetic field/stimulus applied by an outside device (e.g., an electromagnetic transmitter of the tracking system).

At least one retention mechanism 110 may be provided for maintaining a medical device in a predetermined retention position longitudinally along the guidewire body 106. The retention mechanism 110 may act directly upon (e.g., directly contact) the medical device itself and/or the retention mechanism may act in conjunction with one or more other structures to maintain the medical device in the retention position before, during, and/or after a medical procedure using the medical device. The function of the retention mechanism 110 will be discussed in more detail below.

For most use environments, a longitudinal relationship of the retention mechanism 110 to at least one sensor 108 will be known and constant. In such circumstances, one of ordinary skill in the art, provided with a three-dimensional position of the sensor(s) 108, will be able to determine (by association) at least a longitudinal position of the medical device. In most cases, however, knowledge of the three-dimensional position of the sensor(s) 108 will facilitate extrapolation of a three-dimensional position of the medical device held in the retention position and therefore support precise positioning of the medical device as desired with respect to a target site of the patient tissue.

At least one stop structure 112 may be provided in a predetermined stop position longitudinally along the guidewire body 106. The stop structure 112 may be at least partially integrally formed with the guidewire body 106 and/or may be at least partially provided separately and attached to the guidewire body at the stop position. For example, as shown in the Figures, the stop structure 112 is a substantially spherical "bead" attached to the guidewire body 106 near the distal guidewire end 104.

The stop structure 112 could have any desired configuration, size, location, overall shape, cross-sectional shape, material, or any other physical properties as desired for a particular application. For example, as shown in the Figures, the stop structure 112 has a larger maximum lateral stop cross-section (i.e., the outer circumference taken in a lateral cross-section) than a lateral cross-section taken of the guidewire body 106 immediately adjacent the stop structure.

The stop structure 112 may be used, alone or in conjunction with the retention mechanism 110, to block or prevent longitudinal motion of a medical device or other item along the guidewire body 106. Because a longitudinal position of the stop structure 112 along the guidewire body 106 is known with respect to at least one sensor 108, one of ordinary skill in the art will be able to extrapolate, from that known stop structure position, the longitudinal and/or three-dimensional position of another structure contacting the stop structure via the contacting relationship.

An annular connector 114 could be provided on the guidewire body 106, optionally adjacent to or at the proximal guidewire end 102. When present, the annular connector 114 may be connected to at least one position sensor 108 and assist with communicating signals between the sensors 108 and an outside communication device. For example, the annular connector 114 could be a "slip ring" structure laterally surrounding the guidewire body 106. Signals, the exchange of which with the sensors 108 is facilitated by the annular connector 114 may include, but are not limited to, electrical power, electrical information-carrying, magnetic, mechanical, or any other desired type of signal. For example, one or more sensor(s) 108 may be wired, wirelessly, or in any other suitable manner connected for signal transmission to the annular connector 114, which in turn may be wired or wired, wirelessly, or in any other suitable manner connected for signal transmission to the outside communication device.

FIGS. 3-4 illustrate the trackable guidewire apparatus 100 of FIGS. 1-2 incorporated into a surgical navigation system 316. In FIG. 3, the outside communication device is shown schematically at 318 and, as represented by the "lightning bolt" symbol, communicates wirelessly with at least one sensor 108 (one visible in FIGS. 3-4). An annular connector (omitted from FIGS. 3-4 for clarity) could also or instead be used, as described above, to pass signals of any desired type back and forth between the outside communication device 318 and at least one sensor 108. In other examples, the communication between each sensor 108 and the outside communication device 318 can occur via a physical link (e.g., electrically conductive or optical link).

As an example, the attached Appendix discloses example embodiments of a navigation system 316, which includes a tracking system, with which the guidewire apparatus 100 can be utilized. The navigation system of the Appendix thus can generate one or more three-dimensional virtual displays of patient anatomical geometry (e.g, including the geometry of patient vasculature, such as major blood vessels) and the guidewire apparatus 100 in real-time to facilitate intraoperative positioning of the guidewire relative to patient anatomy. The guidewire would correspond to an example of an object that is being tracked and visualized by the positioning system of the attached Appendix.

As also shown in FIGS. 3-4, the surgical navigation system 316 may include an outer sheath 320 having longitudinally spaced proximal and distal sheath ends (distal sheath end shown at 322, proximal sheath end omitted from FIGS. 3-4) separated by a sheath body 324. The sheath body 324 includes a sheath lumen 326 in fluid communication with the proximal and distal sheath ends 322. Optionally, and as shown in FIGS. 3-4, the distal sheath end 322 may taper to a reduced diameter from the majority of the sheath body 324. When present, the outer sheath 320 may be configured to laterally surround an entire cross-section of the guidewire body 106 and longitudinally surround a majority of the length of the guidewire body, for use in facilitating movement of the trackable guidewire apparatus 100 and related structures throughout the patient's body (e.g., through the labyrinthine vascular system).

To use the surgical navigation system 316, a three-dimensional map of a patient lumen (not shown) may be provided. It is contemplated that, for most use environments, that one or more three-dimensional lumen maps may be provided, manipulated, and presented to a user in a virtual manner, such as using a computer with a visual display. (The two-dimensional nature of the visual display will not affect the three-dimensionality of the lumen map.) For example, the three-dimensional lumen map can be generated from a preoperative imaging scan of the patient, such as by using a computed tomography ("CT") scan procedure.

The three-dimensional lumen map may be preoperatively manipulated and enhanced as desired (e.g., colored or filtered to remove extraneous portions), and is contemplated to include an indication of a target site with which a medical device is desired to be associated. For example, in a thermal ablation procedure, the target site could reflect tissue which is to be cauterized with a heat-producing electrode. The description herein, however, for purposes of consistency of example, presumes that the medical device is a self-expanding stent and that the target site is an aortic aneurysm, across which the stent is desired to be placed. It is also contemplated that a positioning system, such as that described in the attached Appendix, may be provided with suitable information about a specific medical device being used with the guidewire system 100 (e.g., physical dimensions, materials, weave/flexibility type, directionality, stiffness, and/or any other desired information) that can assist the positioning system with computations and/or guiding a user to achieve a desired result for that specific medical device.

A "bare" partial trackable guidewire system 100, comprising a portion of a surgical navigation system 316, is shown in FIG. 5A. This schematic view includes the distal guidewire end 104, a portion of the guidewire body 106, two longitudinally spaced sensors 108, a stop structure 112, and a retention mechanism 110. The retention mechanism 110 shown in the Figures includes a collar 528 substantially laterally surrounding a circumference of the guidewire body 106, with a plurality of rotationally spaced barbs 530 extending longitudinally from a distal side of the collar. The barbs 530 and collar 528, or any other suitable retention mechanism 110, may have any suitable structure for performing the functions described herein as desired.

In the embodiment shown in FIGS. 5A-5B, the barbs 530 have some degree of flexibility and are able to pivot (into and out of the plane of the page in FIGS. 5A-5B) about their attachment point to the collar 528. However, it is contemplated that the barbs 530 will normally point in the distal direction, as shown, unless sufficient force is applied to pull the tips of the barbs proximally and thus affect the pivoting motion.

Turning to FIG. 5B, a medical device 532 (shown here as a self-expanding stent) is located in a retention position with respect to the guidewire body 106. The location of the medical device 532 along the guidewire body 106 in the retention position is known, so therefore the medical device can be held in the retention position during movement of the trackable guidewire apparatus 100 and the location in space of the medical device can be interpolated responsive at least partially to the locations of the position sensors 108.

The medical device 532 could be placed and retained in the retention position in any suitable manner. For example, the medical device 532 could be loaded onto a proximal guidewire end 102 and passed/slid along the guidewire body 106 into the retention position (which may be predetermined and/or chosen responsive to an actual position of the medical device with respect to the guidewire body). For example, the stop structure 112 could be used, through direct contact and/or indirectly via some intervening structure, to prevent longitudinal motion of the medical device 532 with respect to the guidewire body 106.

Once the medical device 532 achieves the retention position as desired, the medical device may be maintained in the retention position in any suitable manner, such as directly and/or indirectly through use of the retention mechanism 110. For example, the medical device 532 could be directly engaged with the retention mechanism 110—in the depicted arrangement, at least one barb 530 could be used to "catch" the stent.

As another example of a suitable scheme for maintaining the medical device 532 in the retention position, the outer sheath 320 could be placed around at least a portion of the medical device and/or the guidewire body 106 and maintained in a predetermined sheath position longitudinally along the guidewire body 106, as shown in FIG. 5B. As can be seen in FIG. 5B, at least a distal sheath end 322 of the outer sheath 320 is engaged with the retention mechanism 110 through penetration of at least one barb 530 into the material of the outer sheath 320 from the sheath lumen 326. Optionally, longitudinal motion of the outer sheath 320 in at least a first, distalward direction along the guidewire body 106 before, during, and/or after use of the surgical navigation system 316 is limited through direct or indirect contact between the distal sheath end 322 and the stop structure 112, although the distal sheath end 322 is shown spaced away from the stop structure 112 in the Figures, for clarity.

Optionally, the medical device 532 could be maintained in the retention position through cooperation between the outer sheath 320 and retention mechanism 110. For example, and as shown schematically in FIG. 5B, the medical device 532 could be placed within the sheath lumen 326, before, during, and/or after placement of the outer sheath 320 in the sheath position. When, as in the Figures, the retention mechanism 110 engages at least a portion of the outer sheath 320 to maintain the sheath position, the outer sheath may, in turn, exert at least one of a laterally oriented and a longitudinally oriented frictional force between the sheath lumen 320 and the medical device 532. In other words, though the outer sheath 320 and medical device 532 are shown schematically as being laterally separated in FIG. 5B for clarity of depiction, the outer sheath could instead be relatively tightly fit to laterally urge the medical device 532 into frictional engagement that tends to maintain the medical device in the retention position. In such case, the retention mechanism 110 will assist indirectly with maintenance of the medical device 532 in the retention position by engaging with the distal sheath end 322 as shown.

Once the surgical navigation system 316 has been "loaded" with a medical device 532, as shown in FIG. 5B, the distal guidewire end 104 may be placed into a patient lumen 534 in any desired manner (such as, but not limited to, a surgical cutdown). The distal guidewire end 104 and at least a portion of the guidewire body 106 (contemplated to be a portion of the guidewire body carrying the medical device 532 and at least one position sensor 108) is then advanced through at least a portion of the patient lumen 534.

Continuously and/or periodically, the position of at least one position sensor 108 in three-dimensional space may be determined. For example, a particular position sensor 108 could provide a signal relating/corresponding to its three-dimensional position in space to an outside communication device 318. As another example, the outside communication device 318 could (substantially) continuously or periodically interrogate one or more position sensors 108 for signals relating/corresponding to their positions in three-dimensional space.

It is contemplated that information provided by the sensors 108 to the outside communication device 318 could be either a fully developed indication of the position of that sensor in three-dimensional space or a piece of data/information that does not contain a position indication itself but which contains position-correlating/relative information that is used by the outside communication device to determine the position of that sensor in three-dimensional space and/or a three-dimensional position of at least one position sensor in a coordinate system of an associated tracking system, which could be part of (e.g., residing in) a positioning system shown schematically at 536 in FIG. 5B.

The positioning system 536 could be, for example, similar to the system shown and described in the Appendix forming a portion of the present disclosure. As an example of a possible use scenario, the tracking system, would be part of the navigation system and provide coordinates, based upon sensor-related signals received by the outside communication device 318, to the positioning system (e.g., IOPS computer) to determine and generate a virtual display of the relative position for at least a part of the guidewire apparatus 100 and patient anatomy.

Regardless of how the position of at least one position sensor 108 in three-dimensional space is determined, that sensor 108 position can be used by the outside communication device 318 to determine a relative position of at least one sensor 108 with respect to the geometry (e.g., inner contours) of the patient lumen 534. The term "contour" is used herein to indicate an outline, especially of a curving or irregular figure, in three-dimensional space. For example, the positioning system 536 can employ the sensor position (e.g., provided by a tracking subsystem) to determine and display a real-time, virtual three-dimensional position of one or more parts of the guidewire 100 relative to patient anatomy, such as disclosed in the attached Appendix. For most use environments, positions of multiple sensors 108 will be determined, thus allowing a fairly precise three-dimensional contour and shape of the trackable guidewire apparatus 100 to be ascertained, such as disclosed in the Appendix.

An example of a suitable method for determining a relative position of at least one sensor 108 with respect to the geometry of the patient lumen 534 includes mapping a three-dimensional position in space (e.g., the ambient space of an operating room) of at least one position sensor. A three-dimensional contour of at least a portion of the trackable guidewire apparatus 100 in space is produced responsive to the mapped three-dimensional position in space of at least one position sensor. The three-dimensional contour of the trackable guidewire apparatus 100 can then be correlated with a three-dimensional map of the patient lumen 534, such as the map mentioned above as being produced responsive to preoperative imaging. An example of such a method is disclosed in the Appendix.

Because the retention position of the medical device 532 along the guidewire body 106 is known and is presumed to be constant for most use environments, correlation of the three-dimensional contour of the trackable guidewire apparatus 100 with the three-dimensional map of the patient lumen 534 will allow the three-dimensional position of the medical device 532 within the patient lumen 534 to be determined with a relatively high degree of accuracy. For example, an image of at least a portion of the trackable guidewire apparatus 100 (and optionally the medical device 532) in its correlated position with respect to an image of the patient lumen 534 could be shown to the user on a display.

If, responsive to correlation of the sensor 108 position(s) and the patient lumen 534 map, the medical device 532. is determined to have not yet reached a target site (including a target orientation) with respect to the patient lumen, the position of at least a portion of the trackable guidewire apparatus 100 can be adjusted as desired, with additional three-dimensional positions of the sensor(s) 108 in space being continuously or periodically mapped during the adjustment process. This cycle of adjusting at least a portion of the trackable guidewire apparatus 100 and directly or indirectly checking the three-dimensional position of the medical device 532 may be repeated as desired until the medical device is placed into a predetermined spatial relationship (including at least one of gross and fine positioning and device orientation) with a target site of the patient lumen. For example, at least a portion of the trackable guidewire apparatus 100 could be manipulated to place a stent-type medical device 532 across a lesion in a blood vessel. As another example, at least a portion of the trackable guidewire apparatus 100 could be manipulated to place a cauterizing electrode into a perpendicular relationship with a tumor in the body lumen. One of ordinary skill in the art will be able to provide a suitable surgical navigation system 216, including a medical device 532, for a particular use environment.

Once the medical device 532 has been determined to be at the target site in the patient lumen 534 and/or to have a desired orientation with respect to the target site, the medical device may be used as desired. For example, when the medical device 532 is a prosthetic device like the self-expanding stent shown in the Figures, the medical device may be released from the retention position at the target site.

Optionally, the medical device 532 may be released via manipulation of at least a portion of the retention mechanism 110. For example, if a stent is "sewn" onto the guidewire body 106 with a suture-type retention mechanism, a pull-wire at a proximal guidewire end could be tugged to unravel the sutures and thus release the stent. As another example of a medical device 532 is electromagnetically held to the guidewire body 106, the magnet power could be reduced or removed to release the medical device. As yet another example, and as shown here, an outer sheath 320 could be provided to help protect the medical device 532 and/or facilitate passage of the medical device during travel through the patient lumen 534. When present, the outer sheath 320 could be pulled longitudinally proximally sufficiently to overcome a holding force of the barbs 530 and/or to break a frangible circumference [not shown] of the outer sheath. At least a portion of the outer sheath 320 can then be moved longitudinally proximally to gradually release the self-expanding stent type medical device 532 in a known, "catheter pullback" manner.

Once the medical device 532 has reached one or more target sites within the patient lumen 534 and any desired tasks have been performed, the user may retract the trackable guidewire apparatus 100 and any other related structures of the surgical navigation system 316 from the patient lumen 534 in any suitable manner.

FIGS. 6A-6D depict an example sequence of operation that can be used to supplement or supplant the sequence of FIGS. 5A-5D, and is shown using the trackable guidewire apparatus of FIGS. 1-4. In FIG. 6A, the guidewire body 106 is shown as having already been inserted into the patient lumen 534, distal guidewire end 104 leading, and advanced to a position laterally adjacent to a target site (shown generally at 638), with the assistance of the position sensor(s) 108 and the positioning system 536.

Figure 6B:
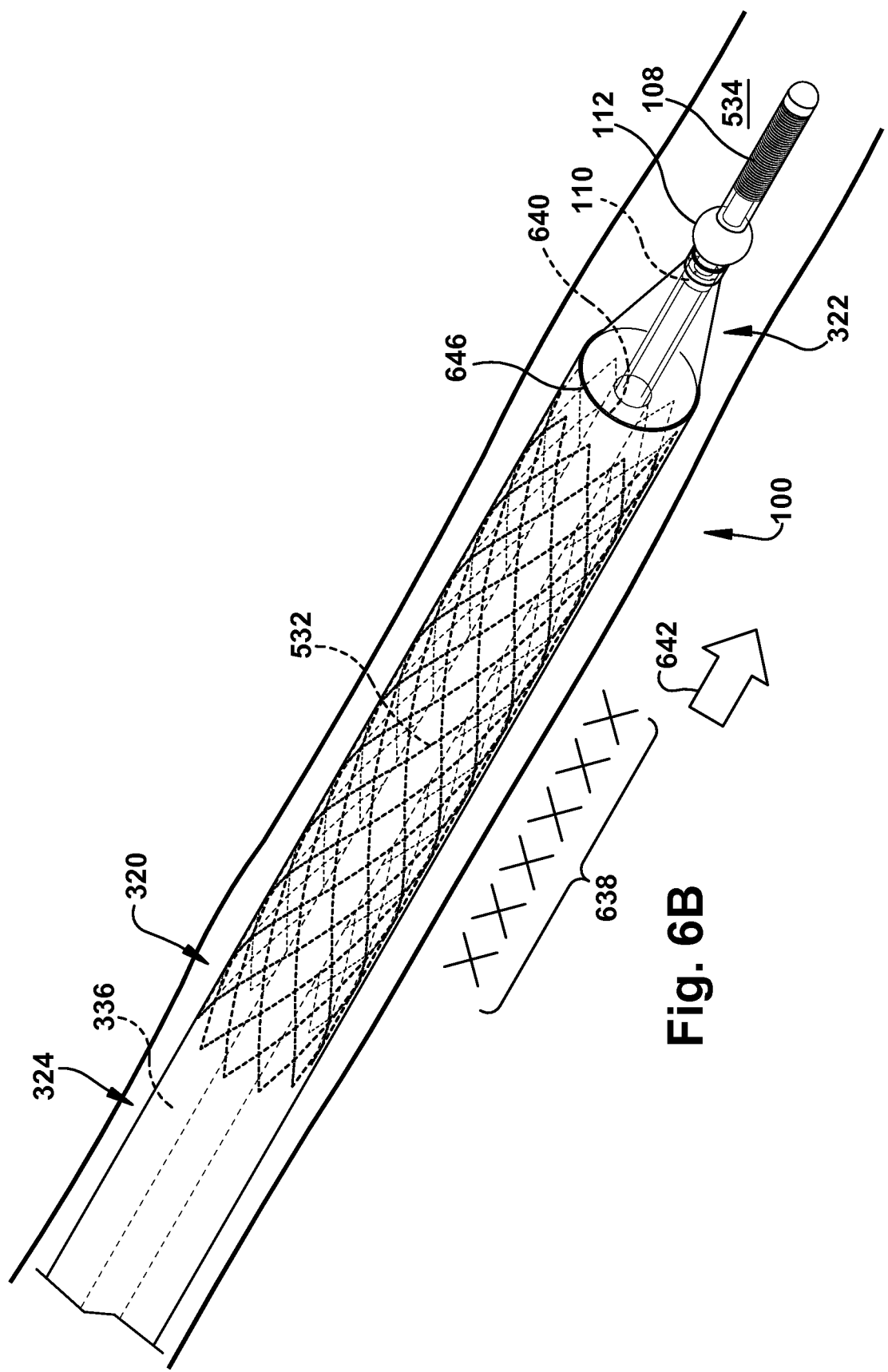
Figure 6C:
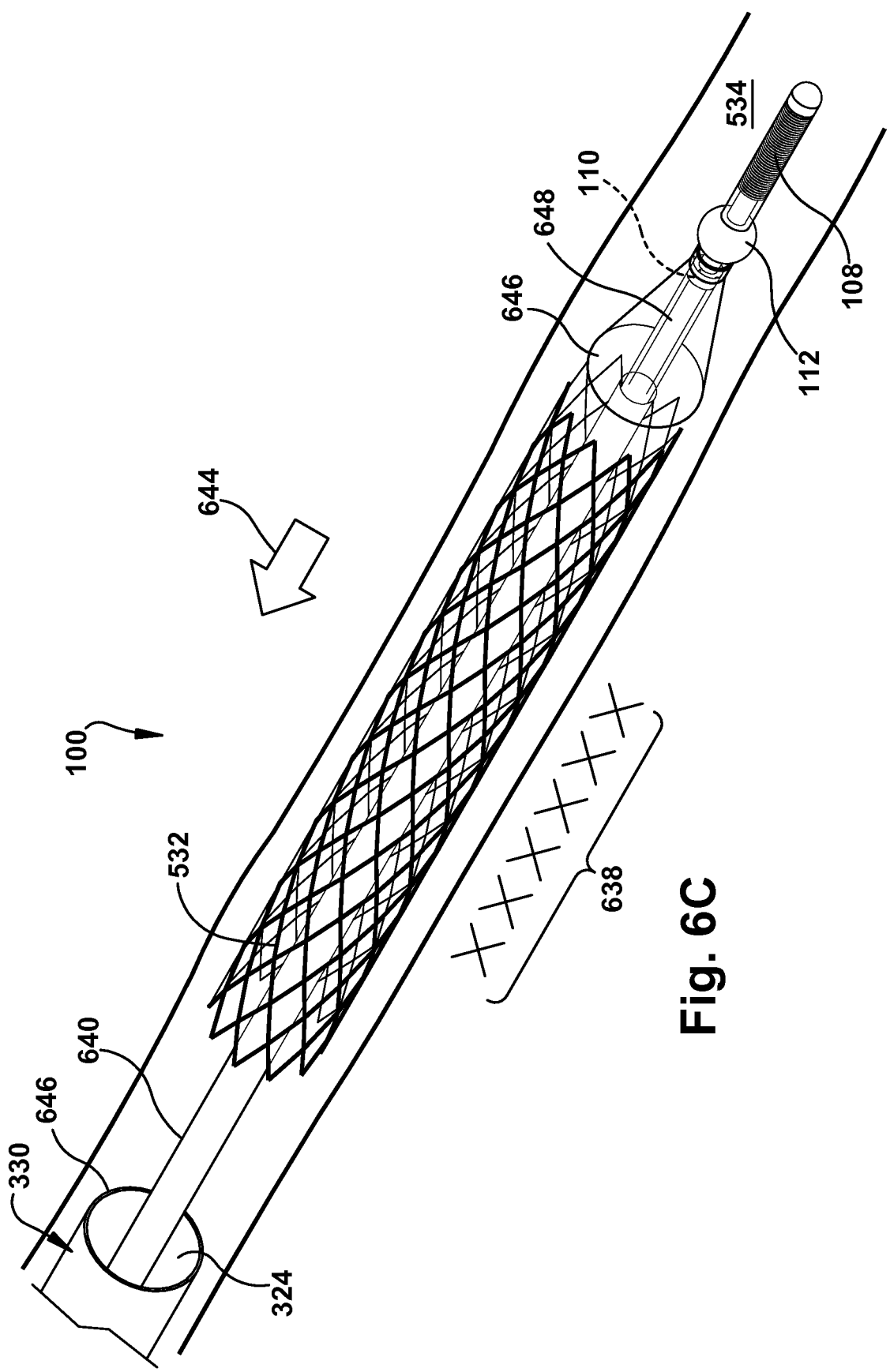
Figure 6D:
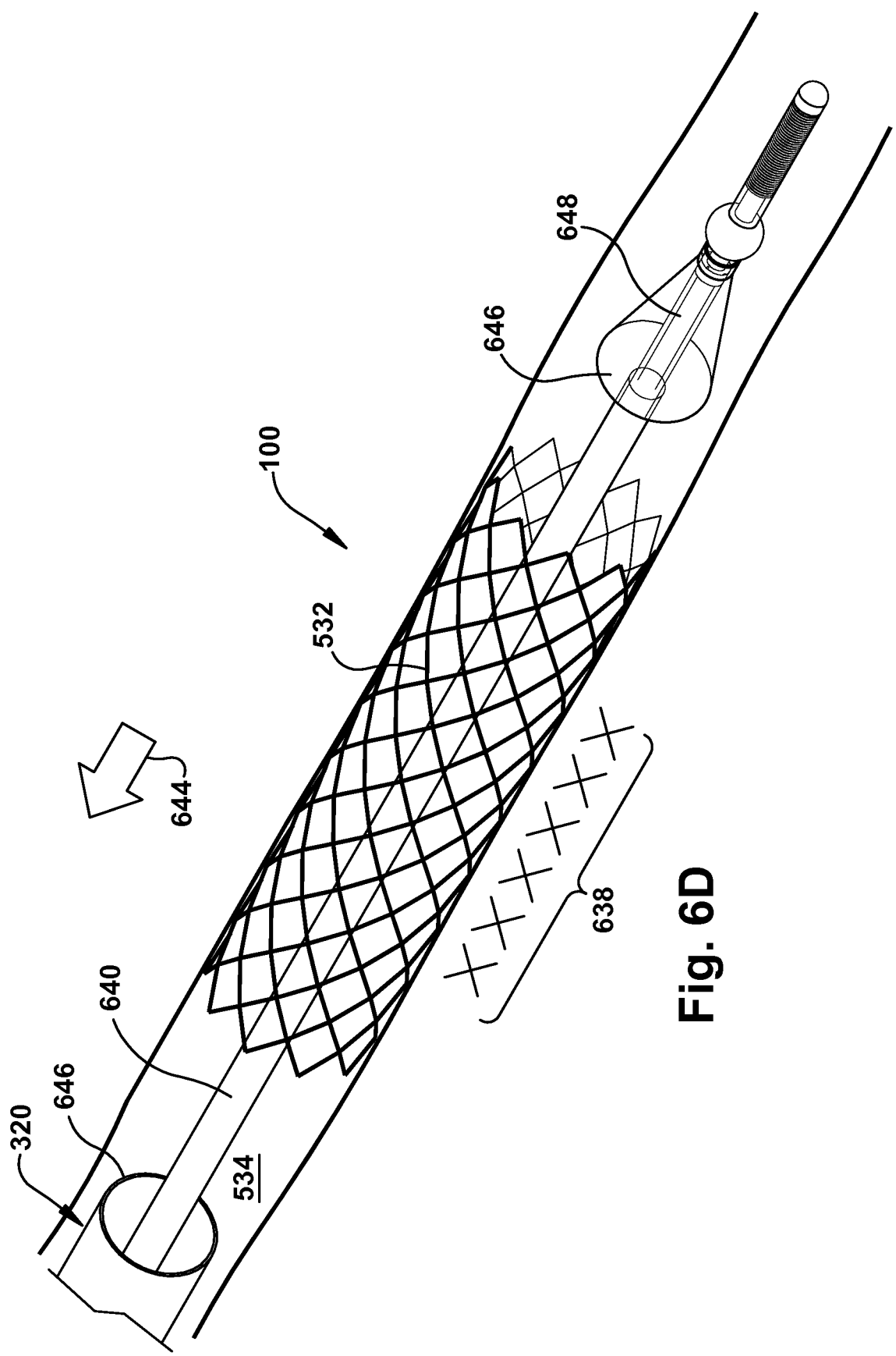

In FIG. 6B, an outer sheath 320, having an inwardly-tapered distal sheath end 322, surrounds a compressed self-expanding medical device 532, such as a stent made at least partially of a shape-memory material. The medical device 532 is compressed inside the sheath lumen 326 for transport. Optionally, and as shown in FIGS. 6B-6D, an inner sheath or rail lumen 640 is located concentrically within the outer sheath 320 and the medical device 532. When present, the rail lumen 640 may closely laterally surround the guidewire body 106 to guide insertion of the outer sheath 320 and medical device 532 in a first direction 642 over the guidewire body 106 and into position at/near the target site 638. The retention mechanism 110 and/or stop structure 112 may physically interact with the rail lumen 640, medical device 532, and/or outer sheath 320 to assist with locating/placing and maintaining the medical device 532 in the predetermined retention position in a desired manner. For example, the retention mechanism 110 could "grab" or "latch onto" at least a portion of the distal sheath end 322 to dictate a position of the medical device 532 (carried in a known relationship within the sheath lumen 326) with respect to the guidewire body 106.

Once the structures of the trackable guidewire apparatus 100 have achieved the relative positions shown in FIG. 6B, the position of the guidewire body 106 may be manipulated slightly to "fine tune" the placement of the retained medical device 532 into the desired position with respect to the target site 638. Whether or not such fine-resolution adjustment occurs, parts of the trackable guidewire apparatus 100 could be manipulated into the position shown in FIG. 6C.

In FIG. 6C, a portion of the outer sheath 320 has been moved distally, in a second direction 644, to retract the outer sheath 320 from about the maintained-in-place guidewire body 106. However, the distal sheath end 322 has been left in place, engaged with the retention mechanism 110, and has been separated from the retracted portion of the outer sheath 320 along release seam 646 (shown in dash-dot line in FIG. 6B and comprising the opposing "cut" ends of the sheath body 324 and a remaining sheath nosecone 648, as shown in FIG. 6C). The release seam 646 is a perforated, reduced-thickness, and/or otherwise frangible portion of the outer sheath 320 structure that separates/breaks in a predetermined manner upon application of a pulling force from the proximal guidewire end. Once the release seam 646 breaks to allow separation of the sheath nosecone 648 from the remaining portion of the sheath body 324, a portion (such as a supermajority) of the outer sheath 320 can be retracted from the patient lumen 534 in the second direction 644. Optionally, the outer sheath 320 can then be discarded (when the outer sheath 320 is disposable or otherwise intended for one-time use), or can instead be re-fitted with a sheath nosecone 648 for later re-use.

Upon removal of the constraining outer sheath 320 from its former laterally-surrounding position about the medical device 532, the medical device 532 will then self-expand into the position shown in FIG. 6D. The portions of the trackable guidewire device (e.g., the rail lumen 640 and guidewire body 106) can then be retracted in the second direction 644 and removed from the patient lumen 534. The medical device 532 can thus be placed into a desired position with respect to a target site 638 with a relatively high degree of accuracy with the assistance of the trackable guidewire apparatus 100.

The release seam 646, when present, may assist with preventing re-use of the outer sheath 320 by destroying the ability of the outer sheath 320 to be assembled with a medical device 532 and rail lumen 640 in the manner pictured in FIGS. 6B-6D. Whether or not the outer sheath 320 is reused, it is contemplated that the guidewire body 106 and attached components (e.g, position sensors 108, stop structure 112, and/or retention mechanism 110) could be reused if desired. The separate provision of a "cartridge"-style subassembly of the outer sheath 320, medical device 532, and rail lumen 640 can provide versatility to the trackable guidewire assembly 100 system by allowing for "cartridges" having different physical properties (e.g., length, width, medical device type/size, stiffness, or the like) to be provided in a library format and selected as desired for a particular surgical procedure. Through use of a library of cartridges, a user is provided with significant choice and flexibility in using the trackable guidewire apparatus 100. In addition, the relatively expensive guidewire body 106 and attached components can be re-used multiple times for a variety of different surgical tasks when fitted for "cartridge" style use, thus reducing the cost-per-use of these more expensive components.

It is contemplated that any or all components of the surgical navigation system 316 discussed herein could be used in conjunction with other stock ("off-the-shelf") or bespoke/custom components/devices to assist with tracking during a surgical procedure. For example, the guidewire body 106 could be a standard, stock guidewire fitted with longitudinally-spaced sensors 108, and optionally stop and retention structures 112 and 110, and used as described above. As another example, a medical device carried by the guidewire body 106 into the patient's body could be a stock stent or stock prosthetic valve which achieves precise placement with the aid of the surgical navigation system 316.

While aspects of this disclosure have been particularly shown and described with reference to the example embodiments above, it will be understood by those of ordinary skill in the art that various additional embodiments may be contemplated. For example, the specific methods described above for using the apparatus 100 are merely illustrative; one of ordinary skill in the art could readily determine any number of tools, sequences of steps, or other means/options for placing the above-described apparatus, or components thereof, into positions substantively similar to those shown and described herein. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Various calculations and determinations are discussed here as being made, and results displayed, to a user via the outside communication device 318, but it is contemplated that any other computer, device, processor, display, or other equipment could be used as desired to provide the described interactive functions between portions of the surgical navigation system 315 for the user. While certain engagements and/or mating relationships between a plurality of structures may be described in various portions of this application as occurring using a tapered/frictional fit component, a hole-and-screw (or other fastener, and/or a set screw arrangement, it is contemplated that any suitable scheme(s) for engaging and/or fastening various structures into the relationships shown here could be used, as desired by one of ordinary skill in the art. Any component of the invention could be provided with a user-perceptible marking to indicate a material, configuration, at least one dimension, or the like pertaining to that component, the user-perceptible marking aiding a user in selecting one component from an array of similar components for a particular use environment. A "predetermined" status may be determined at any time before the structures being manipulated actually reach that status, the "predetermination" being made as late as immediately before the structure achieves the predetermined status. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one embodiment or configuration of the invention could be provided, singly or in combination with other structures or features, to any other embodiment or configuration, as it would be impractical to describe each of the embodiments and configurations discussed herein as having all of the options discussed with respect to all of the other embodiments and configurations. A device or method incorporating any of these features should be understood to fall under the scope of this disclosure as determined based upon the claims below and any equivalents thereof.

Other aspects, objects, and advantages of the invention can be obtained from a study of the drawings, the disclosure, and the appended claims.

Having described the invention, I claim:

1. A method of tracking a position of a medical device relative to a target site of a patient lumen, the method comprising:
   providing a trackable guidewire, the guidewire having longitudinally spaced proximal and distal guidewire ends separated by a guidewire body, the guidewire including a plurality of longitudinally spaced position sensors configured to provide signals corresponding to a three-dimensional position in space to an outside communication device, the guidewire including at least one retention mechanism for maintaining a medical device in a predetermined retention position longitudinally along the guidewire body, and the guidewire including at least one stop structure in a predetermined stop position longitudinally along the guidewire body;
   placing the medical device in the retention position;
   maintaining the medical device in the retention position via the retention mechanism;
   placing the distal guidewire end into the patient lumen;
   advancing the distal guidewire end and at least a portion of the guidewire body through at least a portion of the patient lumen;
   determining a three-dimensional position of at least one position sensor in a coordinate system of an associated tracking system; and
   determining a relative position of the at least one sensor with respect to geometry of the patient lumen.

2. The method of claim 1, including:
   mapping a three-dimensional position of at least one position sensor in a coordinate system of an associated tracking system;
   producing a three-dimensional contour of the guidewire in space responsive to the mapped three-dimensional position of at least one position sensor; and
   correlating the three-dimensional contour of the guidewire with a three-dimensional map of the patient lumen.

3. The method of claim 2, including:
   adjusting a position of at least a portion of the guidewire within the patient lumen responsive to the correlation; and
   placing the medical device into the predetermined spatial relationship with the target site of the patient lumen.

4. The method of claim 1, wherein placing the medical device in the retention position includes preventing, with the stop structure, longitudinal motion of the medical device with respect to the guidewire body.

5. The method of claim 1, wherein maintaining the medical device in the retention position via the retention mechanism includes directly engaging the medical device with the retention mechanism.

6. The method of claim 1, including:
   providing an annular connector on the guidewire body adjacent to the proximal guidewire end;
   connecting the annular connector to the plurality of longitudinally spaced position sensors; and
   with the annular connector, communicating signals between the plurality of longitudinally spaced position sensors and the outside communication device.

7. The method of claim 1, including:
   providing an outer sheath having longitudinally spaced proximal and distal sheath ends separated by a sheath body, the sheath body including a sheath lumen in fluid communication with the proximal and distal sheath ends;
   placing at least a portion of the guidewire body within the sheath lumen; and
   maintaining the outer sheath in a predetermined sheath position longitudinally along the guidewire body.

8. The method of 7, wherein maintaining the outer sheath in a predetermined sheath position longitudinally along the guidewire body includes engaging the outer sheath with the retention mechanism.

9. The method of claim 7, wherein maintaining the medical device in the retention position via the retention mechanism includes the steps of:
   placing the medical device within the sheath lumen; and
   preventing longitudinal motion of the medical device within the sheath lumen via laterally oriented frictional force between the sheath lumen and the medical device.

10. The method of claim 7, wherein maintaining the outer sheath in a predetermined sheath position longitudinally along the guidewire body includes the step of limiting longitudinal motion of the outer sheath in a first direction along the guidewire via the stop structure.

11. The method of claim 1, including releasing the medical device from the retention position at the target site.

12. The method of claim 11, wherein releasing the medical device from the retention position at the target site includes releasing the medical device via manipulation of the retention mechanism.

13. The method of claim 1, wherein the advancement of the distal guidewire end and at least a portion of the guidewire body through at least a portion of the patient lumen occurs before the medical device is placed in the retention position.

14. The method of claim 10, including:
   removing at least a portion of the guidewire body from at least a portion of the outer sheath;
   removing the portion of the outer sheath from which the guidewire body was removed from the patient lumen; and
   discarding the portion of the outer sheath from which the guidewire body was removed.

15. A trackable guidewire apparatus comprising:
   longitudinally spaced proximal and distal guidewire ends separated by a guidewire body;
   a plurality of longitudinally spaced position sensors configured to provide signals corresponding to a three-dimensional position of at least one position sensor in a coordinate system of an associated tracking system in response to an electromagnetic field/stimulus;
   at least one retention mechanism which selectively maintains a separate medical device in a predetermined retention position longitudinally along the guidewire body; and
   at least one stop structure in a predetermined stop position longitudinally along the guidewire body.

16. The trackable guidewire apparatus of claim 15, including an annular connector on the guidewire body adjacent to the proximal guidewire end, the annular connector being connected to the plurality of longitudinally spaced position sensors, the annular connector for communicating signals between the plurality of longitudinally spaced position sensors and an outside communication device.

17. The trackable guidewire apparatus of claim 15, wherein the stop structure has a larger maximum lateral stop cross-section than a lateral guidewire cross-section taken of the guidewire body immediately adjacent the stop structure.

18. The trackable guidewire apparatus of claim 15, wherein the stop structure is integrally formed with the guidewire body.

19. The trackable guidewire apparatus of claim 15, including an outer sheath having longitudinally spaced proximal and distal sheath ends separated by a sheath body, the sheath body including a sheath lumen in fluid communication with the proximal and distal sheath ends, and wherein at least a portion of the guidewire body is selectively placed within at least a portion of the sheath lumen, the distal sheath end being selectively engaged with the retention mechanism, and at least a portion of the outer sheath being selectively manipulated to release the medical device from the trackable guidewire apparatus.

* * * * *